(12) United States Patent
Mueller et al.

(10) Patent No.: US 7,044,927 B2
(45) Date of Patent: May 16, 2006

(54) EXTRACORPOREAL BLOOD TREATMENT SYSTEM

(75) Inventors: Friedrich Mueller, Loehnberg (DE); Sándor Dolgos, Szentendre (HU); Péter Szamkó, Goed (HU)

(73) Assignee: B. Braun Medizintechnologie GmbH, Melsungen (DE)

( * ) Notice: Subject to any disclaimer, the term of this patent is extended or adjusted under 35 U.S.C. 154(b) by 774 days.

(21) Appl. No.: 09/971,031

(22) Filed: Oct. 5, 2001

(65) Prior Publication Data

US 2002/0082728 A1 Jun. 27, 2002

(30) Foreign Application Priority Data

Oct. 5, 2000 (DE) .............................. 100 49 393

(51) Int. Cl.
*A61M 37/00* (2006.01)
*A61M 1/36* (2006.01)
*B01D 61/00* (2006.01)

(52) U.S. Cl. ...................... 604/4.01; 422/44; 210/645

(58) Field of Classification Search ............... 604/6.09, 604/5.01, 6.01, 4.01, 65–67; 422/44, 45; 210/650, 257.1, 258, 645, 646, 739, 195.2; 702/19; 715/733

See application file for complete search history.

(56) References Cited

U.S. PATENT DOCUMENTS

| 5,715,823 | A | 2/1998 | Wood et al. |
| 5,788,851 | A | 8/1998 | Kenley et al. |
| 5,891,035 | A | 4/1999 | Wood et al. |
| 6,551,266 | B1 * | 4/2003 | Davis, Jr. .................. 604/6.09 |
| 6,589,482 | B1 * | 7/2003 | Burbank et al. .............. 422/44 |
| 2003/0154108 | A1 * | 8/2003 | Fletcher-Haynes et al. .... 705/3 |

* cited by examiner

*Primary Examiner*—Patricia Bianco
*Assistant Examiner*—Leslie R. Deak
(74) *Attorney, Agent, or Firm*—Diller, Ramik & Wight

(57) ABSTRACT

An extracorporeal blood treatment system comprises an ECB station with an ECB unit, such as a dialysis machine. Via a web server and a browser, the ECB station communicates with a data net to which external browsers and external web servers are connected. Thus, settings and maintenance operations may be performed on the ECB unit from a remote location. On the other hand, patient-related, machine-related or drug-related data or statistical data or consumption-related data can be transmitted from the ECB station to a remote location. The communication between a user interface, e.g., a touch screen, and the ECB unit is done via the internal browser. Thus, the user interface has access to the data net. The ECB unit receives all data, information and instructions via the web server. Thereby, data of different sources can be processed in the same format and be given different authorizations.

7 Claims, 1 Drawing Sheet

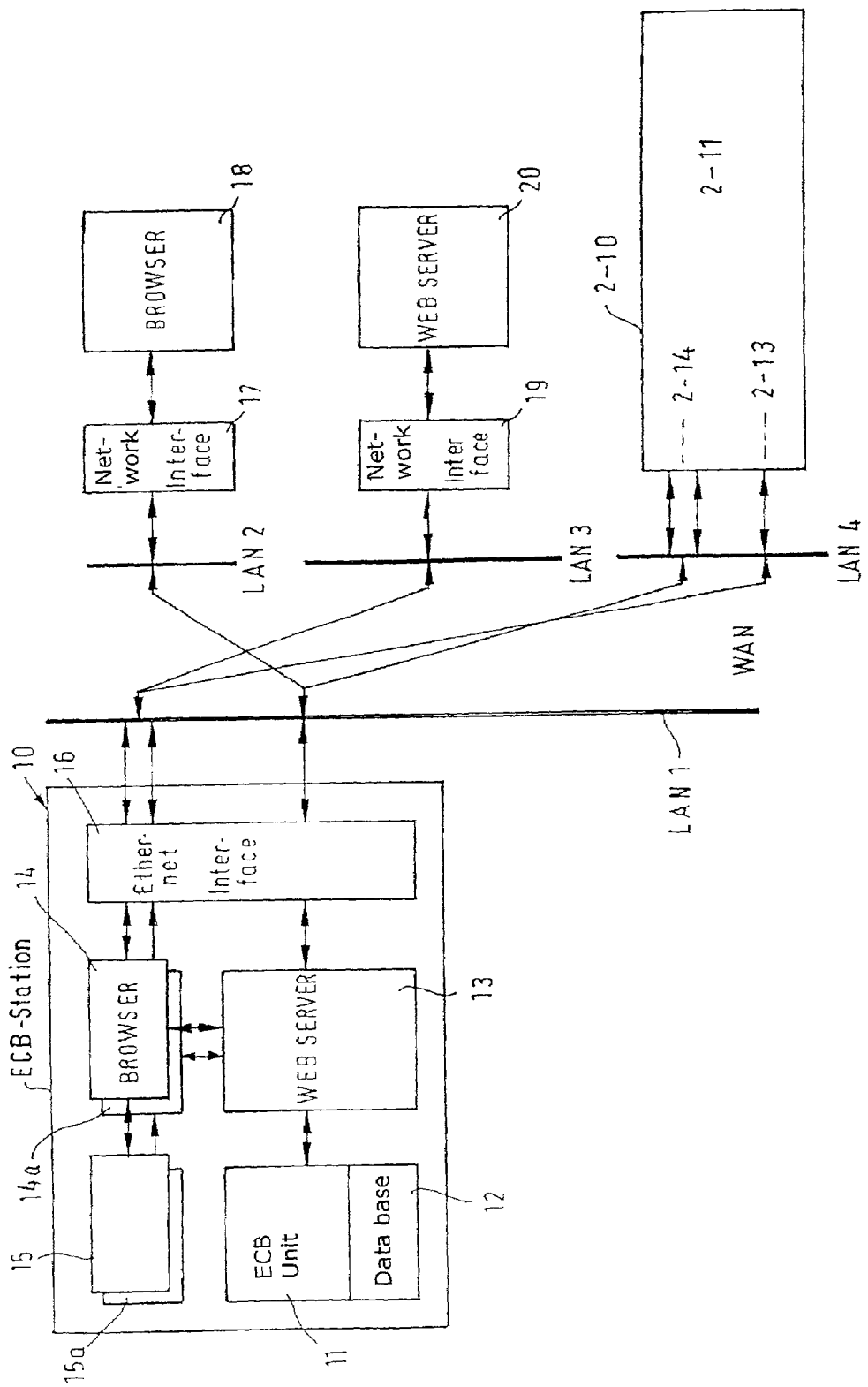

EXTRACORPOREAL BLOOD TREATMENT SYSTEM

FIELD OF THE INVENTION

The present invention refers to an extracorporeal blood treatment system comprising an ECB station (ExtraCorporeal Blood) including an ECB means.

Extracorporeal blood treatment includes, among others, hemodialysis, hemofiltration and hemodiafiltration. Such blood treatment is performed in special machines to which a patient is temporarily connected. Blood is taken from the patient and is passed through a treatment means via an extracorporeal circulation, where after it is supplied back into the patient. Such ECB means are elaborated machines with very complex controls. Depending on the blood treatment to be performed and on the patient-related parameters and on drug-related parameters, different flow rates, ultra-filtration profiles, liquid concentrations and other parameters have to be set and monitored. Additionally, the machine must be monitored for internal or external failures. Operating ECB means requires comprehensive training. The same is true for maintaining and checking ECB units, which requires highly qualified personnel.

ECB means comprise a user interface that may be designed as a touch screen, for example, whereby operating the machine is facilitated. Such an ECB means is described in U.S. Pat. No. 5,788,851.

U.S. Pat. Nos. 5,715,823 and 5,891,035 each describes an ultrasonic diagnosis system, wherein an ultrasonic unit is connected to a data net, e.g. the internet. The ultrasonic unit may be accessed from all points of the data net. Thus, doctors can follow and evaluate an ultrasonic diagnosis even when they are remote from the patient's location. The station where the ultrasonic unit is located includes a browser and a web server as well as the corresponding Ethernet hardware for connection to the data net.

It is an object of the present invention to provide an extracorporeal blood treatment system wherein an ECB means may be accessed both from a user interface and from a remote site, the data transfer being unified and the access control being facilitated.

SUMMARY OF THE INVENTION

An ECB station in accordance with the present invention comprises, besides the ECB means (ECB=extracorporeal blood treatment), an internal web server and an internal browser. The web server is software that provides information about the ECB means such that the information can be transmitted via the data net. The browser is software that controls the data transfer by the web server. The ECB station is configured such that the internal web server can communicate with the internal browser and external browsers of the data net or the browser of another ECB station. As an alternative or in addition, the internal browser may communicate with the internal web server and the external web server or the web server of another ECB station. The particularity of the invention is that the data communication between the user interface and the ECB means is performed via the internal server. That means that the signals of the user interface are converted to the standard of the data net. The internal web server is provided with the signals from the user interface in the same manner and in the same data format as the data from the data net are supplied to the internal web server. As a consequence, the ECB unit receives all signals for inquiries, settings, instructions and other functions from the web server, regardless of whether these data have been provided from an internal or an external source, e.g. an external ECB station.

The invention may be implemented in local data nets. As well as in global data nets. It allows monitoring a plurality of dialysis machines from a central location, for example, using the local data net of a hospital in which a plurality of dialysis machines and the central location are situated. Of course, several hospitals can be connected via a network. On the other hand, the invention also allows for communication via a universal data net, the RCB means having access to a drug data base, for example, containing the data of a plurality of drugs. For example, a specific drug can be associated with an infusion profile having an infusion rate varying in time, the infusion rate having to be adjusted depending on the weight of the patient or other parameters. All these drug-related data could be included in the database accessible by the ECB stations.

Furthermore, it is possible to set up a service center where a skilled service technician monitors the operation of an ECB station and may make adjustments to the machine. Of course, the technician must not interfere with an on-going ECB treatment. Therefore, several authorizations are established, i.e. it is determined in the web server, what priority an instruction has, in this case based on the source of the instruction. Thus, it is possible, for example, that the hospital personnel change the infusion rate at the user interface, but the service technician at a remote location is not authorized to do so. The service technician may work in a service center, for example that has a browser, or he may work at another ECB station or at the ECB station to be monitored.

In the present blood treatment system, the signals from the user interface are raised to the standard of the data nets, as it were, and supplied to the internal web browser and to the internal web server. Thus, all signals, regardless of their source, their origin or their destination, are processed in the same manner, however, different authorizations can be accorded to these signals, as need be.

The invention also allows transmitting other data through the user interface and the browser via the data net, such as x-ray images or patient-related information, so as to provide comprehensive information about the patient to a medicinal capacity present at a remote location and following the blood treatment. For example, an e-mail may be sent through the internal browser.

It is also possible to send software versions or to download these from remote sources.

BRIEF DESCRIPTION OF THE DRAWING

With reference to the sole FIGURE of the drawing, the following is a detailed description of an embodiment of the present invention. The FIGURE illustrates a block diagram of an extracorporeal blood treatment system.

DETAILED DESCRIPTION OF THE INVENTION

The blood treatment system comprises an ECB station 10, which includes an ECB unit 11. The ECB unit 11 may be a dialysis machine including the associated controls, for example, the apparatus available under the trade name "Dialog" from B. Braun Melsungen AG, Melsungen, Germany. The ECB unit 11 is associated with a data base 12. This is a data memory including treatment curves, treatment parameters and machine-related data. The control unit of the ECB means has access to the data base 12.

The ECB unit 11 communicates with the internal web server 13. The web server 13 is an information supply providing information suitable for transfer via the data net. The web server 13 communicates with the internal browser 14. The browser 14 is software for controlling data transfer via the data net. The browser 14 in turn communicates with a user interface 15.This is an input/output device, via which device, a user, i.e. the hospital staff, can input data and instructions, where the output means may be a monitor. For example, the user interface 15 is a touch screen.

The internal web server 13 and the internal browser 14 communicate through a network interface, e.g. an Ethernet interface 16, comprising a data net which, in the present case, is a local data net LAN 1(Local Area Network). The data net LAN 1 may be the data net within a department of the hospital. The local data net itself is part of a global or universal data net WAN (Wide Area Network). In the embodiment, further local nets LAN 2, LAN 3, LAN 4 are provided that are also part of the data net WAN.

An external browser 18 is connected to one of the local data nets LAN 2 via a network interface 17. The term "external" means that the browser is not provided in the ECB unit 10 that is illustrated on the left of the drawing. The external browser 18 communicates with the internal web server 13 via the data nets described to call information or instructions from the same or to enter such into the same. The external browser 18 may be located in a service center of the manufacturer of the ECB unit 11. The service technician may track the current treatment or earlier treatments performed with the ECB unit, and provide technical support or initiate maintenance operations. The external browser 18 only allows for restricted authorization. For example, no interference with an on-going operation of the dialysis machine can be made via the external browser 18.

The external browser 18 may also be located in a central station of the hospital in which the ECB station 10 is operated. Medical staff can thus monitor the treatment, store current or prior treatments and data or record economic performance data, such as material consumption, water or power consumption.

Finally, an external consultant can follow the treatment via the browser 18. In the embodiment, an external web server 20 is connected to the data net LAN 3 via a network interface 19. The web server 20 is located in a work-station. Specific patient parameter sets and/or laboratory data an/or inventory data regarding drugs, filters, disposable articles, etc., may be inputted into the web server. The external web server 20 can also serve to transmit a new software version to the ECB station 10 or to renew or update the contents of the database 12. Finally, the external web server 20 may also be used to accept parameter sets and/or treatment instructions specific to a patient from the ECB station 10.

In the embodiment, a further ECB station 2–10 is connected to the local LAN data net LAN 4, which is designed like the station 10. It has an own internal browser 2–14 and internal web server 2–13 as well as an ECB unit 2–11.

From any point of the global data net, principally, the same data, information and representations may be obtained as on the monitor of the user interface 15. However, because of the different authorizations, some instructions coming from outside will not be executed and certain data will not be displayed.

In the present embodiment, a second user interface 15*a* is provided in addition to the user interface 15, to which interface 15*a* a second browser 14*a* is associated. While the user interface 15 is available to the hospital staff, the user interface 15*a* is provided for use by the patient. The patient may take advantage of the ECB station to use the connected data nets without much additional effort, for example, to send e-mails, do any kind of computer work or have access to the Internet.

What is claimed is:

1. An extracorporeal blood treatment system comprising an ECB station including an ECB means for extracorporeal blood treatment, an internal web server communicating with the ECB means, an internal browser communicating with the internal web server, a user interface communicating with the internal browser, the internal browser being in communication with external web servers over a data net and/or the internal web server being in communication with external browsers via the data net, and the data communication between the user interface and the ECB means is effected through the internal browser.

2. The extracorporeal blood treatment system of claim 1, wherein a central station remote from the ECB station calls and registers treatment parameters, treatment results and/or economically relevant data of the ECB operation via the external browser.

3. The extracorporeal blood treatment system of claim 1, wherein a service station remote from the ECB station calls treatment data or operation data from the ECB station via the external browser.

4. The extracorporeal blood treatment system of claim 1, wherein, from a database remote from the ECB station, machine-related, patient-related or drug-related data are transmitted to the internal browser via a web server.

5. The extracorporeal blood treatment system of claim 4, wherein some of the transmitted data are used to set or vary operation parameters of the ECB means.

6. The extracorporeal blood treatment system of claim 1, wherein the internal web server issues an authorization for parameter settings, information access and control operations depending on the identity of the communicating browser or web server.

7. The extracorporeal blood treatment system of claim 2, wherein a service station remote from the ECB station calls treatment data or operation data from the ECB station via the external browser.

* * * * *